United States Patent [19]

Schneider et al.

[11] 4,117,162
[45] Sep. 26, 1978

[54] NEMATOCIDE CONTROL DIACYLIMIDE CONTROL DIACYLIMIDE COMPOSITIONS

[75] Inventors: Louis Schneider, Elizabeth; David E. Graham, Westfield, both of N.J.

[73] Assignee: GAF Corporation, New York, N.Y.

[21] Appl. No.: 852,513

[22] Filed: Nov. 17, 1977

[51] Int. Cl.² ............................................. A01N 9/20
[52] U.S. Cl. ................................................... 424/320
[58] Field of Search ......................................... 424/320

[56] References Cited

FOREIGN PATENT DOCUMENTS 42-1,313  11/1967  Japan ..................................... 71/118

OTHER PUBLICATIONS

Durrell et al.; J. Org. Chem. vol. 28; 1963, pp. 831–833.

*Primary Examiner*—Allen J. Robinson
*Attorney, Agent, or Firm*—Walter C. Kehm; Walter Katz

[57] ABSTRACT

The invention provides nematocide control diacylimide compositions which include compounds having the formula:

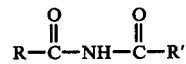

where R and R' are selected from alkyl, alkenyl, haloalkyl and haloalkenyl having from 1–5 carbon atoms, being the same or different groups.

The compositions of this invention show excellent agricultural nematocidal activity, and particularly, the control of endoparasitic and ectoparasitic worms, such as the root knot nematocide, which exist in the soil at some stage of their life cycles.

The diacylimide compounds generally are prepared by reacting a suitable amide with an acyl halide. The acyl halide precursor may be prepared, if necessary, from the corresponding acid by reaction with a suitable halogenating agent, such as thionyl chloride. Similarly, a given amide may be readily prepared, for example, from the corresponding acyl halide by reaction with ammonia.

3 Claims, No Drawings

NEMATOCIDE CONTROL DIACYLIMIDE CONTROL DIACYLIMIDE COMPOSITIONS

BACKGROUND OF THE DISCLOSURE

1. Field of the Invention

This invention relates to novel nematocidal diacylimide compositions which exhibit excellent agricultural nematocidal activity.

2. Description of the Prior Art

Many compositions are known in the literature which are active as nematocides, such as is described, for example, in U.S. Pat. No. 2,909,457. Nematocide compositions relate to the control of endoparasitic and ectoparasitic worms which exist in the soil at some stage of their life cycles, for example, eggs, larvae and adult worms.

The control of nematodes and other parasitic worms in soil is a complex problem. These organisms, either in the egg, larvae or adult stage, are protected by a difficulty permeable membrane. Hence, the effective toxicant must have both the property of penetrating the resistant coatings and the ability to kill. It must also be readily dispersible in soils or other environment of the organism and be stable when incorporated therein. Since the object of ridding soils of nematodes and parasites is to provide a beneficial growth media for plants, the nematocide or parasiticide must not be phytotoxic to plants, or, if phytotoxic, this effect must not be longlived. Such a nematocide, either itself or some phytotoxic decomposition product thereof, should be such that, previous to planting, it is removed from the soil by evaporation, by rain washing or by soil bacterial decomposition.

For the reasons set forth above, completely effective agents for nematodes and other parasitic worm life are not generally available. Furthermore, one skilled in the art cannot predict the effectiveness of compounds as practicable toxicants, even though the physical and biological properties of the compounds are well known.

Since a very careful balance of physical and chemical properties is required in order to provide a chemical substance useful in controlling nematodes and other parasitic worms, this invention has for its principal purpose the provision of compounds which have the above described requisite properties. A further purpose of this invention is to provide a useful method of freeing soils from objectionable nematode life. Other purposes of this invention will be evident from the following specification.

It has now been found that certain diacylimide are very effective as nematocides and as agents for controlling other parasitic worms.

SUMMARY OF THE INVENTION

The invention provides nematocide control diacylimide compositions which include compounds having the formula:

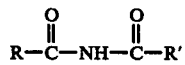

where R and R' are selected from alkyl, alkenyl, haloakly and haloalkenyl having from 1-5 carbon atoms, being the same or different groups.

The compositions of this invention show excellent agricultural nematocidal activity, and particularly, the control of endoparasitic and ectoparasitic worms, such as the root knot nematocide, which exist in the soil at some stage of their life cycles.

The diacylimide compounds generally are prepared by reacting a suitable amide with an acyl halide. The acyl halide precursor may be prepared, if necessary, from the corresponding acid by reaction with a suitable halogenating agent, such as thionyl chloride. Similarly, a given amide may be readily prepared, for example, from the corresponding acyl halide by reaction with ammonia.

DETAILED DESCRIPTION OF THE INVENTION

The nemacidal compounds of the invention are prepared from a suitable amide I which is condensed with an acyl halide II to provide the desired diacylimide compound III, as follows:

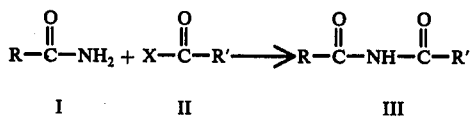

where R and R' are previously defined, and X is a halogen.

Both the acyl halide and amide starting materials usually are commercially available; however, if necessary, the acyl halide may be readily prepared from the corresponding acid by reaction with a suitable acyl halide, such as thionyl chloride. The amide may be readily prepared, for example, from the corresponding acyl halide by reaction with ammonia.

A. Nematocide Activity

The root knot nematode was used as the preferred test subject among some 200 plant parasitic nemas. This nematode is distributed world-wide on a wide assortment of crops. Although it resides in root tissues as a parasite where it incites formation of galls, it may also survive in the soil for many months as a scavenger. The test described below is designed to destroy free living forms and to a lesser extent disinfect gall tissue.

In this test, the air dry soil and sand are blended in a ratio of 2:1 parts; then 6 to 7 grams of chopped galls and root tissues from an infected stock of plants are added to each gallon of mixture. The inoculum then is blended with the mixture and 130 ml. is added to each styrofoam cup (10 oz. size). In the primary test, 10 ml. of a 250 ppm suspension (equivalent to 50 lb/acre) is added to each cup which is then covered with a lid, shaken vigorously 2 hours later to assure uniform distribution, incubated 1 to 2 days, and again shaken. Then the covers are removed and the soil is leveled. Four cucumber seeds are sown in each cup and covered with 30 ml. of sand to a depth of about ¼ inch. The sand is then sprinkled with a nutrient solution (Miracle Gro at 1 Tsp/gal.) containing a damping-off preventative (Dexon at the rate of 1 Tsp of 35% material/gal.) to permit growth of vigorous healthy roots. Three control cups are used, one with inoculum, but no chemical and the other two with a standard nematocide (Dasanit at 25 and 12.5 lb/acre). After 3 or 4 weeks the roots are washed free of soil-sand and rated according to the severity of infection on a scale of 0 (severe galls) to 10 (no infection).

B. Nematocidal Test Data

Table I $$\underset{\|}{R}-\underset{\|}{C}-NH-\underset{\|}{C}-R'$$
$$\phantom{R-}O\phantom{-NH-}O$$

| Compound No. (B-T) | GAF No. | R | R' | Nematocidal Activity Against Root Knot At 25 lb/acre |
|---|---|---|---|---|
| 763 | 7519 | ClCH₂CH₂— | —CCl=CHCl | 9 |
| 427 | 7227 | BrCH₂— | —CCl=CHCl | 5 |
| 367 | 7181 | ClCH₂— | —CCl=CHCl | 8 |
| Control | | Dasanit | | 9.5 |

The following examples will further illustrate the invention without being limiting thereof.

EXAMPLE 1

N-CHLOROACETYL-N-2,3-DICHLOROACRYLOYLIMIDE

A. 2,3-Dichloroacryloylchloride

2,3-Dichloroacrylic acid (211.5g, 1.5 moles), thionyl chloride (357.0g, 3.0 moles), dimethylformamide (7cc) and benzene (300cc) were charged into a 1-liter, 4-neck flask and heated at reflux for 8 hrs. The benzene and excess thionyl chloride were removed atmospherically and 174.5g (73% yield) of product was distilled at 65°–67° C./23mm.

B. 2,3-Dichloroacrylamide

2,3-Dichloroacryloylchloride (174.5g, 1.1 moles) was added to a 3-liter beaker precharged with aqueous ammonia (266cc, 4.4 moles) and ice (500cc). The mixture was stirred for ½ hr. at 0°–5° C., filtered and washed with cold water yielding 135g of amide (88%), m.p. 135°–136° C.

Anal: Calc'd for $C_3H_3Cl_2NO$: Cl, 50.71; N, 10.0. Found: Cl, 50.07; N, 9,69.

C. N-Chloroacetyl-N-2,3-Dichloroacryloylimide

Toluene (150cc), 2,3-dichloroacrylamide (52.0g, 0.37 mole) were charged into a 500 cc, 4-neck flask. Then chloroacetyl chloride (42.0g, 0.37 mole) was added and the reaction mixture was heated at reflux for 22 hrs. The mixture was cooled to 25° C. and the product filtered, washed with cold toluene and vacuum dried yielding 51g (63.8%) m.p. 99°–100° C.

Anal: Calc'd for $C_5H_4Cl_3NO_2$: Cl, 49.14; N, 6.47. Found: Cl, 49.16; N, 6.20.

EXAMPLE 2

N-3-Chloropropionyl-N-2,3-Dichloroacryloylimide

Toluene (100cc), 2,3-dichloroacrylamide (14.0g, 0.1 mole) and 3-chloropropionyl chloride (12.6g, 0.1 mole) were reacted and worked-up in a similar fashion as described in Example 1 to yield 13g (56.6%) of product, m.p. 76°–77° C.

Anal: Calc'd for $C_6H_6Cl_3NO_2$:Cl, 45.35; N, 6.10. Found: Cl, 45.63; N, 6.02.

EXAMPLE 3

N-Chloroacetyl-N-Propionylimide

Toluene (100cc), propionamide (7.3g, 0.1 mole) and chloroacetyl chloride (11.3g, 0.1 mole) were reacted and worked-up in a similar fashion as described in Example 1 to yield 5.5g (37.2%) of product of m.p. 169°–170° C.

Anal: Calc'd for $C_5H_8ClNO_2$:Cl, 23.7; N, 9.36. Found: Cl, 23.6; N, 9.52.

EXAMPLE 4

N-Bromoacetyl-N-3-Chloropropionylimide

Toluene (100cc), 3-chloropropionamide (10.7g, 0.1 mole) and bromoacetyl chloride (20.2g, 0.1 mole) were reacted and worked-up in a similar fashion as described in Example 1 to yield 15.5g (71.6%) of product m.p. 133°–134° C.

Anal: Calc'd for $C_4H_7BrClNO_2$ Total halogen (Br, Cl) 50.5; N,6.13. Found: Total Halogen (Br, Cl) 50.2; N, 6.25.

EXAMPLE 5

N-Acryloyl-N-Chloroacetylimide

Methylene chloride (150cc), chloroacetyl chloride (62.1g, 0.55 mole) and acrylamide (35.5g, 0.5 mole) were stirred at 25°–30° C. for 25 hrs. The product was filtered, washed with cold methylene chloride and dried to yield 17.0g (23.1%) of product, m.p. 175°–176° C.

Anal: Calc'd for $C_5H_6ClNO_2$:Cl, 24.0; N,9.49. Found: Cl, 24.8; N, 9.26.

EXAMPLE 6

N-Bromoacetyl-N-2,3-Dichloroacryloylimide

Toluene (100cc), 2,3-dichloroacrylamide (14.0g, 0.1 mole), and bromoacetyl chloride (20.2g, 0.1 mole) were reacted and worked-up in a similar fashion as described in Example 1 to yield 15.5g (59.4%) of product, m.p. 121°–122° C.

Anal: Calc'd for $C_5H_4BrCl_2NO_2$ Total Halogen (Br, Cl) 57.9; N,6.14. Found: Total Halogen (Br, Cl), 58.8; N, 5.78.

In those diacylimides listed in Table I which contain an unsubstituted alkenyl group it is preferable to obtain these compounds by dehydrohalogenation of the corresponding haloalkenyl group, as for example, by refluxing with triethyl amine. A typical preparation according to this procedure is described in the following example.

EXAMPLE 7

BIS-(ACRYLOYL) IMIDE

A. Bis-(3,3′-dichloropropionyl) imide

3-Chloropropionyl chloride (256.0g, 2.0 mole) was charged to a 1 liter, 4-neck flask equipped with a stirrer, thermometer and reflux condenser and heated to 80°–85° C. Acrylamide (115.0g, 1.6 mole) and hydroquinone (0.8g) was added and the reaction manufactured at 90°–100° C. for ½ hour. The reaction mixture was cooled to 75° C. and poured with good stirring into 350cc cold chloroform. The product was filtered cold and air dried yielding 87.0g (43.9%), mp 146°–147° C.

Anal: Calc'd for $C_6H_9Cl_2O_2N$:Cl, 35.9; N, 7.0. Found: Cl, 35.6; N, 6.9.

B. Bis-(acryloyl) imide

Acetone (300 cc) and Bis(3,3′-dichloropropionyl) imide (25.0g, 0.13 mole) were added to a 1 liter 3-neck flask equipped with a stirrer, dropping funnel, reflux condenser and thermometer. Tiethylamine (30.0g, 0.30 mole) in acetone (75 cc) was added over 45 minutes and the reaction mixture stirred at 25°–30° C. overnight.

The triethylamine hydrochloride was filtered and the acetone concentrated by rotory evaporation with the temperature being maintained below 40° C. The product was filtered, washed with acidified (pH$_2$) deionized water, and dried under vacuum yielding 7.5 g (41.4%) of product, m.p. 178°–179° C.

Anal: Calc'd for C$_6$H$_7$O$_2$N: N, 11.2. Found: N, 10.9.

WE CLAIM:

1. A method of controlling nematode-infested soil which comprises applying to the nematode a nematocidally effective amount of a diacylimide compound having the formula:

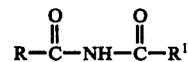

wherein R and R$^1$ being the same or different are selected from the group consisting of alkyl, alkenyl, haloalkyl and haloalkenyl groups having from 1–5 carbon atoms.

2. A method according to claim 1 in which said compound is N-chloroacetyl-N-2,3-dichloroacryloylimide.

3. A method according to claim 1 in which said compound is N-3-chloropropionyl-N-2,3-dichloroacryloylimide.

* * * * *